(12) United States Patent
Bonelli et al.

(10) Patent No.: US 8,083,725 B2
(45) Date of Patent: Dec. 27, 2011

(54) DISPOSABLE ABSORBENT ARTICLES WITH IMPROVED GARMENT FASTENING

(75) Inventors: Guido Bonelli, Pescara (IT); Remo Bellucci, Spoltore (IT)

(73) Assignee: The Procter & Gamble Company, Cincinnati, OH (US)

( * ) Notice: Subject to any disclaimer, the term of this patent is extended or adjusted under 35 U.S.C. 154(b) by 407 days.

(21) Appl. No.: 12/144,944

(22) Filed: Jun. 24, 2008

(65) Prior Publication Data

US 2009/0018518 A1    Jan. 15, 2009

(30) Foreign Application Priority Data

Jul. 13, 2007   (EP) .................................. 07112434

(51) Int. Cl.
*A61F 13/15* (2006.01)
(52) U.S. Cl. .................... 604/391; 604/389; 604/387
(58) Field of Classification Search .................. 604/391, 604/389, 387
See application file for complete search history.

(56) References Cited

U.S. PATENT DOCUMENTS

| | | | |
|---|---|---|---|
| 4,894,060 A * | 1/1990 | Nestegard ..................... | 604/391 |
| 4,959,265 A | 9/1990 | Wood et al. | |
| 5,547,531 A | 8/1996 | Allen et al. | |
| 5,614,232 A * | 3/1997 | Torigoe et al. ................ | 425/545 |
| 5,615,460 A | 4/1997 | Weirich et al. | |
| 5,647,864 A | 7/1997 | Allen et al. | |
| 5,762,645 A | 6/1998 | Peck et al. | |
| 7,344,525 B2 | 3/2008 | Linker, III et al. | |
| 7,444,722 B2 | 11/2008 | McDaniel et al. | |
| 7,579,514 B2 | 8/2009 | Arora et al. | |
| 7,811,272 B2 | 10/2010 | Lindsay et al. | |
| 2003/0120251 A1 | 6/2003 | Couture et al. | |
| 2004/0102745 A1 | 5/2004 | Means | |
| 2005/0148984 A1 | 7/2005 | Lindsay | |
| 2005/0241119 A1 | 11/2005 | Efremova et al. | |

FOREIGN PATENT DOCUMENTS

| | | |
|---|---|---|
| EP | 0 140 135 A1 | 5/1985 |
| EP | 0 476 992 B1 | 7/1995 |
| EP | 145627 | 5/2004 |
| SE | A-374489 | 3/1975 |
| WO | WO 98/10728 | 3/1998 |
| WO | WO 00/61054 | 10/2000 |
| WO | WO 2007/050195 | 5/2007 |

OTHER PUBLICATIONS

PCT International Search Report dated Nov. 5, 2008.

* cited by examiner

*Primary Examiner* — Jacqueline F Stephens
(74) *Attorney, Agent, or Firm* — Andres E. Velarde; Amanda T. Barry; David M. Weirich

(57) ABSTRACT

A disposable absorbent article with an element intended to absorb bodily exudates and a web with stems which functions as a mechanical fastener to prevent shifting of the article e.g. when affixed on underwear.

13 Claims, 3 Drawing Sheets

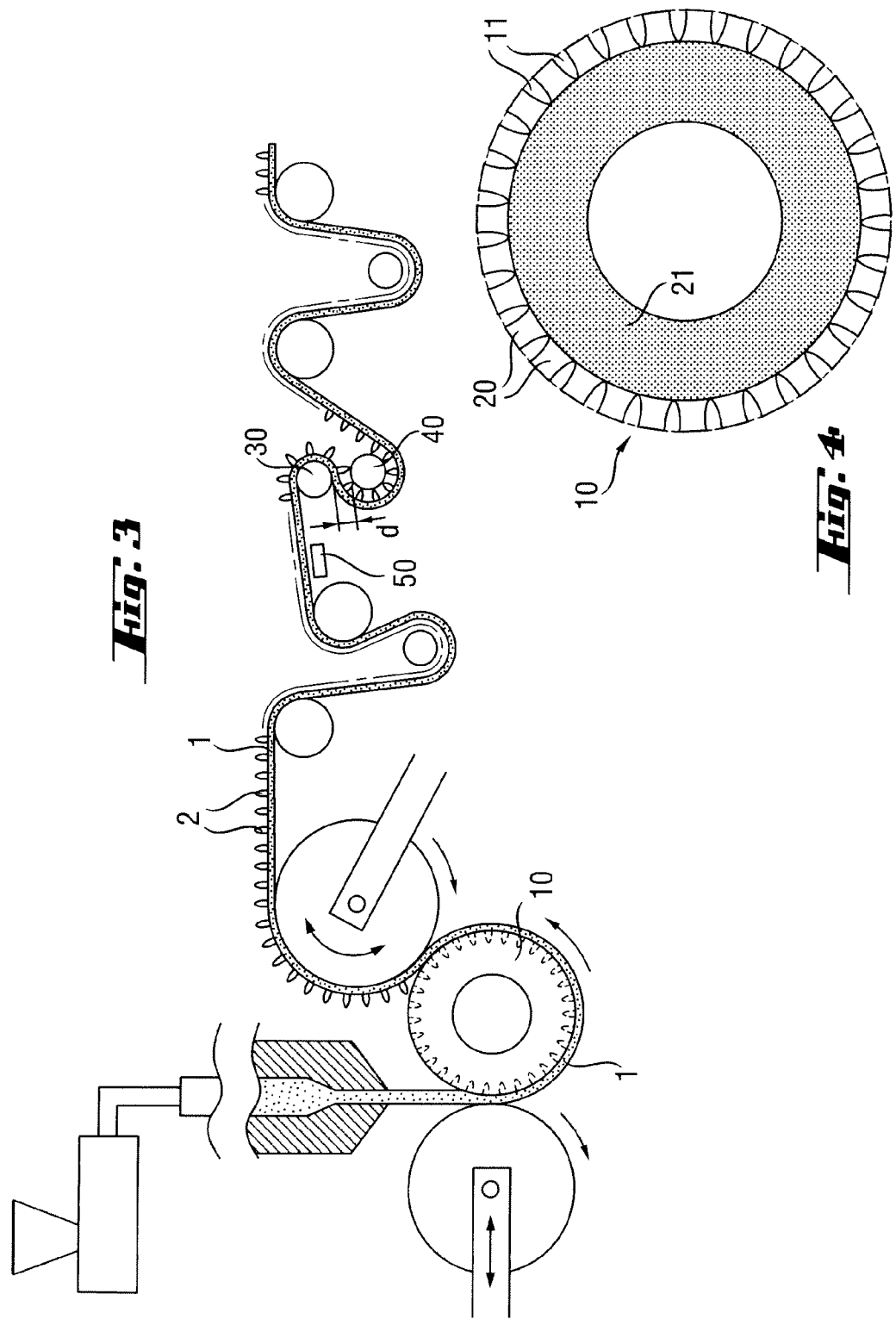

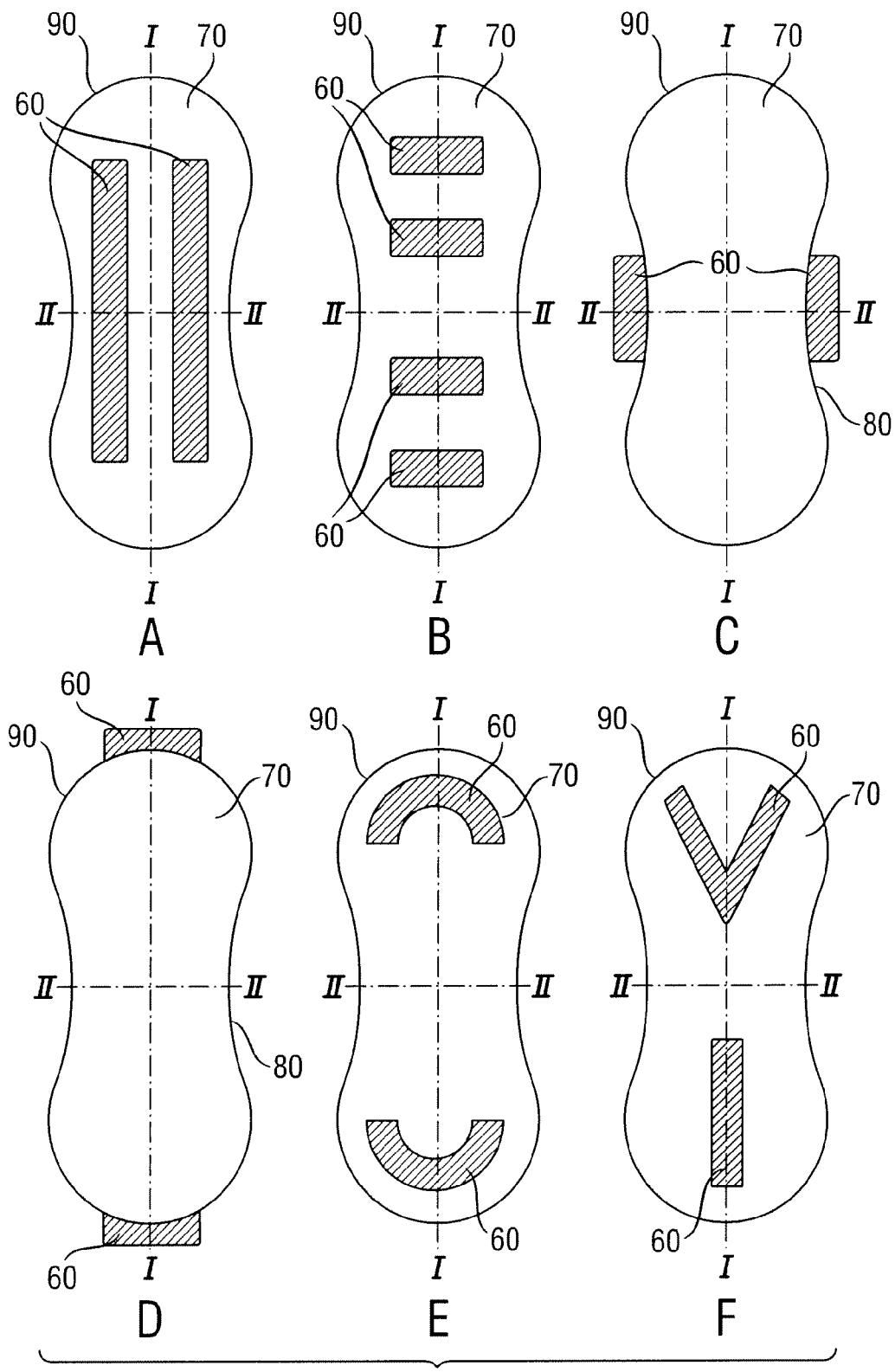

DISPOSABLE ABSORBENT ARTICLES WITH IMPROVED GARMENT FASTENING

FIELD OF THE INVENTION

The present invention relates to absorbent articles for personal hygiene, especially sanitary napkins, panty liners, diapers, incontinence products and the like. More particularly, the present invention relates to articles which, once applied on a garment, have a reduced tendency to shifting during use.

BACKGROUND OF THE INVENTION

Hygienic absorbent articles such as for example sanitary napkins and pantyliners are often formed by a liquid permeable topsheet, a liquid impermeable backsheet and an absorbent core positioned between the topsheet and the backsheet. The backsheet is usually provided with an area comprising a pressure sensitive adhesive (PSA) for securing the disposable absorbent articles to the users' undergarments.

In particular, the use of hot melt and emulsion-based adhesives is general technical standard. The application of emulsion-based adhesives onto the backsheets of absorbent articles for garment fastening is for instance known from SE-A-374,489. The use of hot melt adhesives for this purpose is for instance described in EP-A-140,135 or in WO 00/61054.

The user of these articles normally releases the adhesive (by unwrapping the article from its package and/or removing an adhesive release sheet) and applies the article on the panties in its correct position. PSA can be provided at various adhesive strength, but normally a PSA which has a weak adhesion on the panties is used so to ensure that panties are not damaged upon removal of the article, as well as to avoid that adhesive residues are left. This has the side effect that absorbent articles may not stay perfectly in place during use, especially if the person wearing them is moving a lot e.g. by having a sport session. In some cases absorbent articles may shift from their intended position thus reducing their protective effect and possibly causing staining on panties or underwear. In order to limit this problem it has been proposed to combine mechanical fasteners with conventional PSA.

Mechanical fasteners for this application have been described e.g. in U.S. Pat. No. 4,959,265 by 3M which describes a pressure-sensitive adhesive tape fastener, the backing of which has an array of bluntly pointed stems protruding beyond the pressure-sensitive adhesive. The stems are able to penetrate woven fabrics or other foraminous substrates thus offering a higher resistance to shifting than conventional PSA.

However the fastener described in U.S. Pat. No. 4,959,265 still is not completely satisfactory in terms of grip and of safety on the garment. In fact the stems are quite short and the rugosity of their surface is not controlled.

Therefore there is a need for improved absorbent articles which incorporate an improved fastening mean which provide better stay in place and better safety on garments.

SUMMARY OF THE INVENTION

The disposable absorbent article of the present invention comprises an element intended to absorb bodily exudates and a web with stems, said web with stems comprising a base strip and at least one stem projecting from said base strip and forming part thereof, said at least one stem having a straight axis and a cross section perpendicular to said straight axis which is constant or decreasing from the base to the top of the stem, said web with stem being characterized in that the at least one stem has a height, measured along its straight axis, and a width, corresponding to its largest dimension measured parallel to a plane defined by the base strip, said width being comprised between 0.05 mm and 0.250 mm, and the ratio of the height to the width (H/W) being greater than 2.

BRIEF DESCRIPTION OF THE DRAWINGS

FIG. 3 is an overall view of a production apparatus for making the web with stems; and FIG. 4 shows, the moulding roller of the apparatus of FIG. 3.

FIG. 5 shows several exemplary embodiments of absorbent articles according to the invention.

DETAILED DESCRIPTION OF THE INVENTION

Figure 1:
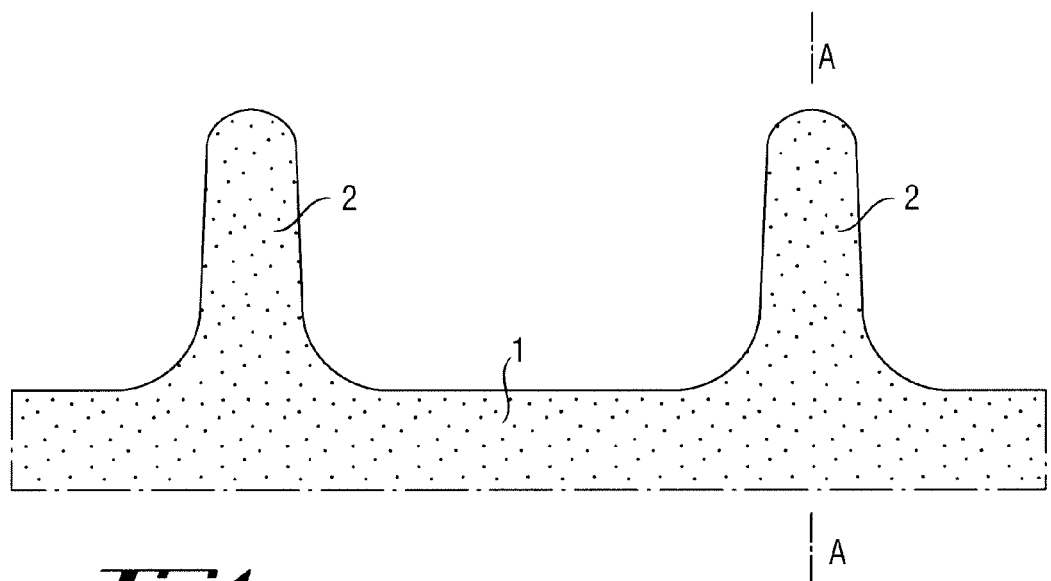
FIG. 1 is a side view of a web with stems to be employed in articles according to the invention.

The term 'absorbent article' is used herein in a very broad sense including any article being able to receive and/or absorb and/or contain and/or retain fluids and/or exudates, especially bodily fluids/bodily exudates. The absorbent article, which is referred to in the present invention typically comprises a fluid pervious topsheet as the wearer-facing surface, a fluid impervious backsheet as the garment-facing surface that is typically water vapour and/or gas pervious and an absorbent core comprised there between. Furthermore, absorbent articles in the context of the present invention are provided with a means for their attachment to the user's garment, in particular with an adhesive. Absorbent articles in the context of the present invention are disposable absorbent articles. Typical disposable absorbent articles according to the present invention are absorbent articles for personal hygiene, such as baby care articles like baby diapers; incontinence pads and perspiration pads like underarm sweat pads or hat bands. Typical disposable absorbent articles are absorbent articles for feminine hygiene like sanitary napkins and panty liners and incontinence pads.

By "bodily exudate" or "body fluid" it is meant herein any fluid produced by the human body including for instance perspiration, urine, blood, menstrual fluids, vaginal secretions and the like.

The term 'disposable' is used herein to describe articles, which are not intended to be laundered or otherwise restored or reused as an article (i.e. they are intended to be discarded after a single use and conventionally to be recycled, composted or otherwise disposed of in an environmentally compatible manner).

The term 'use', as used herein, refers to the period of time that starts when the absorbent article is actually put in contact with the anatomy or in clothing of the user and that lasts until removal of the absorbent article for disposal.

The term "stem" as used herein refers to an elongated protrusion. Each stem has a straight longitudinal axis and a cross section, perpendicular to the longitudinal axis, that is constant or decreasing from the base to the top of the stem. Stems can penetrate a fabric among the threads, without grasping to them, as opposed to an "hook", like those used in Velcro® which is a protrusion terminating with a hook which can penetrate a fabric but it grasps to the threads.

The term "conical" as used herein refers to a shape which cross section measured along a cross section perpendicular to the axis of the shape, goes decreasing towards its top portion.

The present invention aims to overcome the drawbacks of the prior art by proposing disposable absorbent articles comprising an element intended to absorb bodily exudates and a web with very fine stems and which can be used to provide an anti-slip function which is particularly efficient on a fabric without damaging it. Such webs with stems can be obtained by the method and the apparatus described herein.

The disposable absorbent articles of the present invention comprise an element intended to absorb bodily exudates and a web with stems, the web with stems comprises a base strip and at least one stem projecting from the base strip and forming part thereof, the stem having a straight axis and a cross section perpendicular to the straight axis which is constant or decreasing from the base to the top of the stem, the stem having a height, measured along its straight axis, and a width, corresponding to its largest dimension measured parallel to the plane of the article, the width being comprised between 0.05 mm and 0.250 mm, and the ratio of the height to the width (H/W) is greater than 2 or, in other embodiments, greater than 3.

In some embodiments stems may be of the same material as the strip and may be integral with the strip. In certain embodiments the web is made of thermoplastic material.

In one embodiment the web may take the form of a ribbon comprising at least one stem. The ribbon is attached by any known mean on the backsheet of the disposable absorbent articles so that the at least one stem is protruding from the backsheet surface.

According to a development of the invention, the height of the at least one stem may be between 0.3 mm and 0.8 mm, or between 0.4 mm and 0.6 mm. The width of the at least one stem may be between 0.05 mm and 0.250 mm, or between 0.15 mm and 0.23 mm.

In one embodiment, the strip has a thickness measured along the axis of said at least one stem which may be less than 0.1 mm, in other embodiments is between 0.03 mm and 0.09 mm.

In certain embodiments at least a tip section of the at least one stem is conical. In other embodiments said at least one stem comprises a first lower conical section and at least a second upper conical section, particularly a conical tip section, of which the conicity (defined by its upper half angle) is greater than that of the first section, in particular being between 3° and 20°. This at least double conicity ensures particularly efficient action of the anti-slip effect.

According to another development of the invention the at least one stem may comprise a first straight cylindrical lower section and at least a second conical upper section, particularly a conical tip section, the conicity of which (defined by its upper half angle) may be between 3° and 20°.

According to another embodiment of the invention, the at least one stem may have a free end in the shape of a dome, particularly spherical, and particularly with a radius of curvature between 0.025 mm and 0.080 mm, or between 0.033 mm and 0.054 mm.

In some embodiments, the axis of said at least one stem may be inclined respective to the plane of the strip with an angle comprised between 70° and 110°, in other embodiments this angle is substantially equal to 90°.

In certain embodiments, at least a part of the external surface of said at least one stem, particularly the top part of said at least one stem, may have a rugosity measured under the Standard ISO (Ra or average deviation of rugosity, i.e. the arithmetical average of all the Y coordinates of the profile in a base length) of less than 400 nm. In other embodiments rugosity may be less than 300 nm, or less than 250 nm.

In other embodiments, at least a part of the external surface of said at least one stem, in particular a top part of said at least one stem, may have a statistical rugosity (Rms) less than 450 nm. In other embodiments statistical rugosity may be less than 350 nm, or less than 275 nm.

A rugosity or a statistical rugosity within mentioned ranges provides absorbent articles comprising web with stems according to the present invention which are particularly delicate on fabrics and thus do not cause damage to the underwear.

In certain embodiments the web with stems comprises more than one stem and said more than one stem can be arranged in rows, circles, geometric figures or can be randomly disposed over the surface of the base strip. In some embodiments stems can occupy only one or more portions of the surface of the base strip leaving other portions of the surface of the base strip free of stems. In particular the web with stems may be in the form of a ribbon wherein the stems are arranged in rows parallel to the longest dimension of the ribbon. In some cases the areas with stems arranged in parallel rows may be alternated with areas wherein the stems are not present.

In some embodiments stems may be distributed over one or more portions of the surface of the web with stems with a density within said portions of from 1 stem/cm$^2$ to 500 stem/cm$^2$. In other embodiments the density may be from 10 to 300 stems/cm$^2$ or from 20 to 200 stems/cm$^2$.

In certain embodiments a traditional pressure sensitive adhesive can be applied on the web with stems within the stems and/or over areas which are free of stems. This allows to combine the effect of a traditional glue and of the web with stems to further improve the stay in place of the articles while reducing the amount of glue employed.

An embodiment of the invention will now be described solely by way of example by reference to the drawings, in which only the portion of the article including stems is represented:

FIG. 1 is showing a section of a web with stems in the longitudinal direction (that is to say in the direction in which the strip is produced from the machine), comprising a strip or base 1 of a thermoplastic material, for example polyolefin, such as polyethylene or polypropylene for example or similar, from which stems 2 of the same material project, forming part of the strip 1. The stems 2 have a lower section of low conicity, the half angle at the tip being around 3° (this section could also be straight) and an upper conical section, of which the half angle at the tip is 15°. It could also be between 3° and 20° for example. The stems are arranged in rows and columns. The spacing of a row, that is to say the distance between two successive stems in a row, can preferably be less than the spacing of the columns. In particular, the rows can extend as a sinusoid with limited curvature, allowing greater efficiency of introduction of the stems into a fabric in certain applications.

In certain embodiments the height of the stem may be between 0.300 and 0.800 mm, or between 0.400 and 0.600 mm.

The width of the stems at the base may be between 0.100 and 0.200 mm and may be different if measured along the machine direction (direction of unrolling of the strip and direction in which the stretching is carried out) or measured along the transverse direction (CD direction), in some embodiments in fact the cross-section of the stem may be slightly oval.

In some embodiments the ratio of the height to the width of the stem at its base may be greater than 2. In other embodiments, the ratio may be greater than or equal to 3 or 4.

The thickness of the strip excluding the stems is between 0.02 mm and 0.15 mm, or, in other embodiments, between 0.03 and 0.09 mm.

Such web with very fine stems can be obtained by using the apparatus and the method herein described. An apparatus for manufacturing webs with stems is known in the art. According to the prior art, a moulding roller is provided which comprises cavities of a complementary form to the stems which one wishes to obtain. Thermoplastic material is passed in a liquid or melted state on the surface of the roller, so that it is introduced into the cavities and, after cooling, a web having stems of a complementary form to that of the cavities is obtained on leaving the apparatus. The cavities in prior art methods are formed by laser etching in a supple material such as rubber. These method and apparatus have the following drawback. By reason of the formation of the stems through moulding, and particularly by reason of the fact that it is necessary to extract these stems from their cavity after their formation in the cavities, it may be difficult to obtain webs with stems that are very fine and of big height. This is in particular true in the cases of conical stems.

It is also difficult to obtain stems that have all a substantially identical height. Finally, it is very difficult, by reason of the manufacturing tolerances linked to the laser etching in rubber, to obtain webs with stems which are very close to each other at least in one direction.

A new and improved apparatus and method is used herein for producing web with stems according to the invention. The apparatus comprises a forming roller, in which cavities are formed of a shape complementary to the shape of the stems to be formed, and is characterized in that the forming roller, at least in part is made of a porous material with open pores, particularly in the form of a layer, whereby the porosity is chosen so that air molecules can pass but molecules of thermoplastic material cannot, whereby the arrangement is such that the part of a porous material delimits the cavity at least partially, particularly a section at the bottom thereof.

As a consequence of this improved construction for the molding apparatus, the air which, in the known apparatuses, was trapped in the bottom of the cavities by the thermoplastic material, is now expelled through this porous material, thus allowing the thermoplastic material to reach the bottom of the mold thus allowing to obtain stems which are simultaneously fine and of big height.

The forming roller may comprise at least one upper layer in a first material and one lower layer in a second material, whereby the first material can be hollowed out or machined and the second material is of a porous material, the cavities being formed through hollowing-out or machining in the first material until it is flush with the second material which thus forms at least a section of the bottom.

The lower layer may consist of the roller itself (with the exception of the upper layer in the first material), for example may consist of the hub of the roller, which can be made of porous ceramics.

Thus, when the web with stems is formed by introducing thermoplastic material into the cavities, particularly with a fluidity index, at the time of the entry of the material into the cavity, between 9 and 150 g/10 min, the flux of this material is not slowed down by the trapped air which can escape through the porous material. As a result, the melted or liquid thermoplastic material, even in the case of a very fine and/or very deep cavity, can reach the bottom of the cavity, and the stems obtained after extraction have dimensions approximately equal in height to the depth of the cavity.

The machining or hollowing-out may be made by laser etching, the external surface of the lower layer serving as arrest surface for the laser beam, for example with a periscopic finder, in which the laser beam is deactivated (it receives by reflection too much energy) when it reaches the surface of the second material.

The porosity is chosen in such a way that the pores have an equivalent diameter (diameter of the circular cross-section of the same cross-section as that of the pores) of less than 50 micrometers.

The cavities are moulded through machining of the material by micro piercing, particularly of a layer of a plastic material, or by electro erosion, particularly of a layer of metallic material.

The combination of the use of the porous material and the machining through electro erosion or micro piercing allows stems to be obtained which are particularly fine and of great height, also with great reproducibility, whereby the final height of the stems corresponds to almost exactly that of the cavities.

Furthermore, the shape of the cavities can be selected at will. In particular, one can now obtain stems having a cylindrical lower part and at least one upper part in the shape of a cone, and at the same time being nonetheless very fine and of a big height.

The device for forming a web with stems, having on leaving the forming roller a first thickness, a first length and a first width, comprises an upstream roller and a downstream roller disposed one after the other in the direction of the length (machine direction), the downstream roller having a rotating speed greater than that of the upstream roller, the distance between the two rollers being small, in such a way that the web, on leaving the forming device, has a second thickness which is smaller than the first thickness and a second length which is greater than the first length. Furthermore, it has a width substantially identical to the first width.

Through this device, one obtains very fine stems with a big height, in combination with a very thin base. In one embodiment the downstream roller could be cold, that is to say at a temperature below the softening temperature of the stretched thermoplastic material, for example being of the order of 25° C., and the upstream roller may be hot, that is to say at a temperature which is equal to or greater than the softening temperature (Vicat point) of the thermoplastic material of the web.

It is thus possible to obtain, after the cold downstream roller, a strip of which the width may vary a little or not at all along its length. The variability of the width of the final strip is thus clearly improved with respect to the prior art.

The inter-roller distance is preferably equal to around one times the total thickness of the web with stems i.e. typically between 0.5 mm and 10 mm, for example between 0.7 mm and 3 mm.

The web with stems may be subjected to heating on the side of the strip opposite the stems, prior to the stretching.

Figure 2:
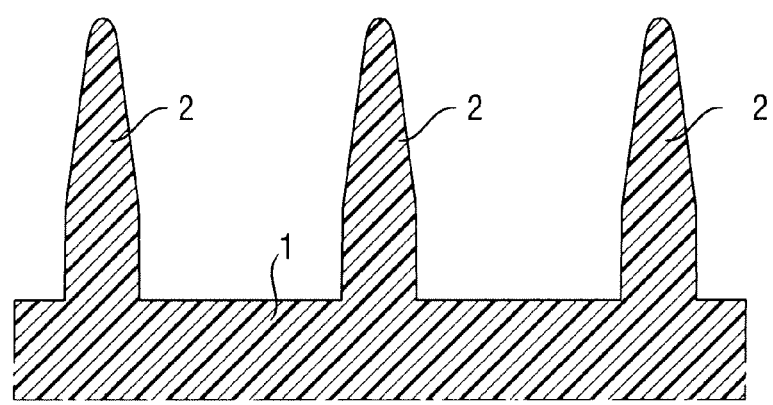
FIG. 2 is a view of a cross-section along the line A-A of FIG. 1.

FIG. 3 shows a production apparatus for a web with stems which can be used in articles according to the invention. Liquid or melted thermoplastic material is passed into a moulding roller 10 comprising cavities 11 of cylindrical conical form, complementary to the form of the stems (such as those of FIGS. 1 and 2) which one wishes to obtain on leaving the apparatus. The material passes around the moulding roller, between the latter and a pressure roller which presses the melted material into the cavities in excess. After being removed from pressure and cooling, possibly by a supplementary cooling device, a web is obtained with a strip of a thickness corresponding essentially to the interstice between the two rollers and stems with a form corresponding almost exactly to that of the cavities.

On leaving the roller, it is also provided to stretch the web with stems in one direction, particularly in the machine direction or unrolling direction of the web, whereby this is in accordance with so-called "short" stretching.

On leaving the moulding roller, the web with a stem thus formed passes between a first roller 30, so-called upstream roller, and a second roller 40, so-called downstream roller. The downstream roller is set in rotation at a speed greater than that of the upstream roller in order to thus stretch the web in its longitudinal direction. "Short" stretching is intended to mean that the distance d between the two rollers is small and corresponds essentially to the initial total thickness of the web with stems.

A heating device 50 is disposed upstream of the upstream roller 30 and preheats the back of the unrolled web in order to facilitate the stretching.

The speed of the first roller is greater than 2 to 4 times the speed of the second roller. In particular, it can be between 1 and 25 meters per minute. The upstream roller 30 is heated to a temperature greater than or equal to the softening temperature (Vicat point) of the thermoplastic material and the downstream roller 40 is cold, that is so say below this softening temperature).

A particularly supple strip is thus obtained and with stems cooperating perfectly well with a fabric in order to ensure an anti-slip function. Besides, the variability of the width of the strip obtained along its length is very small, even zero.

The moulding roller 10 is shown in section in FIG. 4. The roller comprises an outer annular peripheral layer 20 of a material which can be etched by laser, particularly a rubber, particularly heat hardenable, or by micro piercing, particularly a plastic material, or by electro erosion, particularly a metal. The surface and the cavities can then be non-stick treated, particularly by a silicone varnish. This layer is in contact with a lower layer 21, also annular and of a material which is sufficiently hard to resist laser etching, for example being of stainless steel or copper. However, this material is realized so as to be permeable to air and impermeable to the usual thermoplastic material, whereby the material is so-called micro-porous material with open pores of a diameter of less than 0.050 mm. A material of this type is for example a porous stainless steel SIKA-R 100 IS which is available from GKN Metals Filters under the reference Seamless Filter tube 316L.

Thus, when producing the moulding roller, the cavities can be formed by laser by etching the material of the outer layer until the lower layer is reached, where the etching is "stopped". The lower layer will thus form a section of the bottom of the cavity and when the thermoplastic material is pressed into the cavity, even in the case of a very fine conical cavity, it is not prevented from reaching the bottom by an accumulation of air at the bottom, whereby the air is evacuated by the pores of the porous material. Very fine conical stems can thus be obtained.

The web with stems can be incorporated into conventional disposable absorbent articles in any manner available to the skilled man. For example in one embodiment substantially all the backsheet of the disposable absorbent article is covered or replaced by the web with stems. Alternatively, in case the outer layer of the backsheet is a fibrous web, the web with stems can be placed inside the absorbent article, below the outer layer, with stems protruding out of the outer layer.

In other exemplary embodiments, some of which are shown in FIG. 5, a number of separate portions of the web with stems (60) of the present invention can be applied onto the backsheet (70) or along the periphery (80) of the absorbent articles (90). These portions of web with stems can be applied onto the backsheet using any currently known technique, such as by adhesive lamination, ultrasonic welding, thermobonding and so on. In one example shown in FIG. 5A, two portions of the web with stems (60) having the shape of a ribbon can be applied on the backsheet (70) of the article along a direction substantially parallel to the longitudinal direction (I) of the absorbent article (90). In another example shown in FIG. 5B several portions of the web with stems (60) in the form of a ribbon are applied along a direction perpendicular to the longitudinal direction (I). In the third and fourth examples shown in FIG. 5C and D, portions of the web with stems (60) are applied along the periphery (80) of the article (90) outside its borders. In the fifth example shown in FIG. 5E two portions of the web with stems (60) which are cut in a curved shape are applied on two longitudinally opposite portions of the backsheet (70) of the article (90). In the sixth example shown in FIG. 5F portions of the web with stems (60) having a V shape and a linear shape are combined. Of course many other absorbent articles comprising a web with stems according to the present invention can be provided by the skilled man following the teaching of the present application.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising an element intended to absorb bodily exudates and a web with stems, the web with stems comprising a base strip and at least one stem having a base and a top projecting from the base strip and forming part thereof, the at least one stem having a straight axis and a cross section perpendicular to the straight axis which is constant or decreasing from the base to the top of the stem, the at least one stems also having a height, measured along its straight axis, and a width, corresponding to its largest dimension measured parallel to a plane defined by the base strip, the width being between about 0.05 mm and about 0.250 mm, and the ratio of the height to the width being greater than about 2; wherein a tip section of the at least one stem is conical; and wherein the stems penetrate a fabric without grasping to a thread of the fabric.

2. An article according to claim 1 wherein the at least one stem is made of the same material as the strip.

3. An article according to claim 1 wherein the height of the at least one stem is between about 0.3 mm and about 0.8 mm.

4. An article according to claim 1 wherein the width of the at least one stem is between about 0.05 mm and about 0.250 mm.

5. An article according to claim 1 wherein the base strip has a thickness measured along the axis of the at least one stem which is less than about 0.1 mm.

6. An article according to claim 1 wherein the at least one stem comprises a first lower conical section and at least a second upper conical section, of which the conicity, defined by its upper half angle, is greater than that of the first section.

7. An article according to claim 1 wherein the at least one stem comprises a first straight cylindrical lower section and at least a second conical upper section, of which the conicity, defined by its upper half angle, is between about 3° and about 20°.

8. An article according to claim 1 wherein the at least one stem has a free end in the shape of a dome, particularly spherical, and particularly with a radius of curvature between about 0.025 mm and about 0.080 mm.

9. An article according to claim 1 wherein the strip defines a plane and the axis of the at least one stem is inclined respective to the plane of the strip with an angle comprised between about 70° and about 110°.

10. An article according to claim 1 wherein the at least one stem has an external surface and at least a part of the external surface of the at least one stem has a rugosity measured under the Standard ISO Ra less than about 400 nm.

11. An article according to claim 1 wherein at least a part of the external surface of the at least one stem has a statistical rugosity Rms of less than about 450 nm.

12. A disposable absorbent article comprising an element intended to absorb bodily exudates and a web with stems, the web with stems comprising a base strip and at least one stem having a base and a top projecting from the base strip and forming part thereof, the at least one stem having a straight axis and a cross section perpendicular to the straight axis which is decreasing from the base to the top of the stem, the at least one stem also having a height, measured along its straight axis, and a width, corresponding to its largest dimension measured parallel to a plane defined by the base strip, the width being between about 0.05 mm and about 0.250 mm, and the ratio of the height to the width being greater than about 2; wherein a tip section of the at least one stem is conical; and wherein the stems penetrate a fabric without grasping to a thread of the fabric.

13. An article according to claim 12 wherein the at least one stem having a base and a top projecting from the base strip and forming part thereof, having a cross section perpendicular to the straight axis which is decreasing from the base to the top of the stem, the at least one stem also having a height, measured along its straight axis, and a width, corresponding to its largest dimension measured parallel to a plane defined by the base strip, the width being between about 0.05 mm and about 0.250 mm, and the ratio of the height to the width being greater than about 2; wherein a tip section of the at least one stem is conical; and wherein the stems penetrate a fabric without grasping to a thread of the fabric.

* * * * *